United States Patent [19]
Lohwasser

[11] Patent Number: 5,670,693
[45] Date of Patent: Sep. 23, 1997

[54] DITHIOCARBAMATE SALTS AND THEIR USE AS VULCANIZATION ACCELERATORS

[75] Inventor: Hermann Lohwasser, Dormagen, Germany

[73] Assignee: Bayer AG, Leverkusen, Germany

[21] Appl. No.: 679,018

[22] Filed: Jul. 12, 1996

[30] Foreign Application Priority Data

Jul. 27, 1995 [DE] Germany ............ 195 27 437.7

[51] Int. Cl.$^6$ ............................. C07C 255/29
[52] U.S. Cl. ............... 558/303; 558/436; 562/26; 525/351; 525/352; 526/288
[58] Field of Search ............. 558/303, 436; 562/26; 526/288; 525/351, 352

[56] References Cited

FOREIGN PATENT DOCUMENTS

| 40 37 756 | 6/1991 | Germany. |
|---|---|---|
| 226836 | 3/1926 | United Kingdom. |
| 1143956 | 2/1969 | United Kingdom. |

OTHER PUBLICATIONS

Orbit Abstract of DE 40 37 756 (Jun. 6, 1991).
Winfield Scott, *Disubstituted Guanidines*, Industrial and Engineering Chemistry, vol. 15, No. 3, pp. 286–290, Mar. 1923.
*Chemisches Zentralblatt*, 94, Jahrgang, Band II, Seite 261 (1923) & *India Rubber Journal*, Band 64, Nr. 2/12 (1922), Seite 937.

*Primary Examiner*—Johann Richter
*Assistant Examiner*—Ebenezer Sackey
*Attorney, Agent, or Firm*—Connolly & Hutz

[57] ABSTRACT

Salts of formula (III)

$$\begin{array}{c} R_1 \\ \diagdown \\ N\!-\!\!\!\!=\!\!\!\!\begin{array}{c}S\\ \\ S^{\ominus}\end{array} \cdot H_2N^{\oplus}\!\!=\!\!C\begin{array}{c} N\!-\!R_2 \\ | \\ R_3 \\ \diagdown \\ N\!-\!R_2 \\ | \\ R_3 \end{array} \end{array} \quad (III)$$

wherein $R^1$ represents CN or a $C_1$–$C_8$ alkyl group, $R_2$ a mononuclear $C_6$–$C_{10}$ aryl group and $R_3$ a $C_1$–$C_3$ alkyl group or hydrogen; and of formula (IV)

$$\begin{array}{c} R' \\ \diagdown \\ CH\!-\!NH\!-\!CS_2^{\ominus} \\ | \\ CH\!-\!NH\!-\!CS_2^{\ominus} \\ \diagup \\ R'' \end{array} \cdot 2\,H_2N^{\oplus}\!\!=\!\!C\begin{array}{c} N\text{-Aryl} \\ | \\ R \\ \diagdown \\ N\text{-Aryl} \\ | \\ R \end{array} \quad (IV)$$

wherein R represents hydrogen or $C_1$–$C_3$ alkyl, Aryl a $C_6$–$C_{10}$ (substituted) phenyl group, and R', R" represent hydrogen and $C_1$–$C_4$ alkyl or R'+R" together represent $C_4$ alkylene and a process for their preparation by reaction of the thiocarbamate of a primary aliphatic amine, of a bis-amine or of cyanamide with a guanidine hydrohalide.

4 Claims, No Drawings

DITHIOCARBAMATE SALTS AND THEIR USE AS VULCANIZATION ACCELERATORS

Vulcanization accelerators are used in addition to sulphur for the vulcanization of unsaturated rubbers. A group of these accelerators are the dithiocarbamates of formula (I), based on secondary amines

wherein $R_1$ and $R_2$ represent a $C_1$–$C_6$ alkyl group, $R_2$ also a $C_6$–$C_{10}$ aryl group and $Me^+$ represents a monovalent ammonium cation or the equivalent fraction of a multivalent metal cation (e.g. ½ $Zn^{++}$, ¼ $Te^{++++}$)

Another group which also are suitable are the strongly basic diarylguanidines of formula (II)

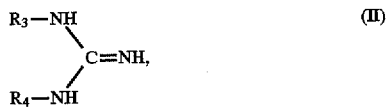

wherein $R_3$ and $R_4$ represent $C_6$–$C_{10}$ aryl groups.

During the vulcanization of rubber, vulcanization accelerators based on secondary amines can form nitrosamines by cleavage and reaction with nitrogen oxides or nitrite, since nitrogen oxides are present as traces in the air and also in constituents of the rubber stock, for example in the form of nitrite as impurity. Many nitrosamines are regarded as carcinogenic, so that their appearance during the vulcanization is undesirable.

The object of the invention is to provide compounds that can be used as accelerators for the vulcanization of rubber without the risk of nitrosamine formation.

The invention consequently provides salts from monoalkyldithiocarbamate or alkylenebisdithiocarbamate anions and N,N'-diarylguanidyl cations. These salts can be represented by formulae (III) and (IV).

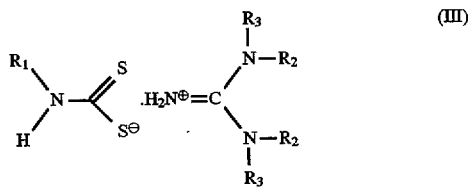

In formula (III), $R_1$ represents a $C_1$–$C_8$ alkyl group or -CN (nitrile group), $R_2$ a $C_6$–$C_{10}$ aryl group (preferably phenyl) and $R_3$ a $C_1$–$C_3$ alkyl group or hydrogen.

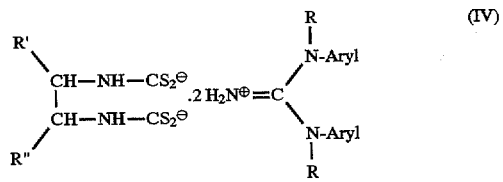

In formula (IV),

R', R" represent hydrogen or a $C_1$–$C_6$ alkyl group or an alkylene chain formed by ring closure, R represents hydrogen or a $C_1$–$C_3$ alkyl group and Aryl a $C_6$–$C_{10}$ aryl group (preferably phenyl).

These salts can be obtained simply by reaction of an aqueous solution of an ammonium or alkali metal dithiocarbamate or bisdithiocarbamate with an aqueous solution of a diarylguanidine hydrohalide or of a dialkyldiarylguanidine hydrohalide. The salt then precipitates and may be separated off and dried conventionally.

This reaction may be carried out at room temperature or also at temperatures up to 80° C. Generally, stoichiometric quantities of the starting materials are used in order to obtain almost stoichiometric yields and to leave none of the starting products over at the end of the reaction.

Examples of suitable starting products are those derivatives of alkyldithiocarbamates or of alkylenebisdithiocarbamates and arylguanidine hydrohalides that yield the lowest possible total molecular weights, especially potassium N-methyldithiocarbamate sodium ethylene 1,2-bisdithiocarbamate sodium propylene 1,2-bisdithiocarbamate ammonium butylene 2,3-bisdithiocarbamate dipotassium N-cyanodithiocarbamate N,N'-diphenylguanidine hydrochloride N,N'-di-o-tolylguanidine hydrochloride N,N'-dimethyl-N,N'-diphenylguanidine hydrogen sulphate.

In the vulcanization process and in their vulcanizate properties the compounds prepared therefrom are equivalent to the known heavy-metal dialkyldithiocarbamates, as for example zinc diethyldithiocarbamate or zinc dibenzyldithiocarbamate, and technically superior to all simple dialkylammonium dithiocarbamates of secondary amines still customary today. Thus, the "internal" combination of diarylguanidine with singly N-substituted dithiocarbamates is really the suitable nitrosamine-free replacement for the "classical" metal dithiocarbamates.

EMBODIMENTS a) 1 mol sodium monomethyldithiocarbamate ("Metam-natrium") and 1 mol diphenylguanidine hydrochloride (DPG-HCl) are reacted together as aqueous solutions at 20° C. A crystalline precipitate is formed, which corresponds to a compound of formula (IIIa)

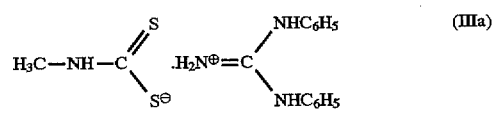

b) In the same way as under a), 1 mol disodium ethylenebisdithiocarbamate ("Nabam") and 2 mol DPG-HCl are reacted. In this way, (IVa) is produced quantitatively

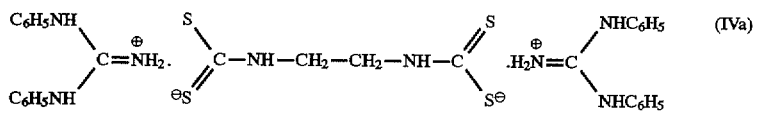

c) In the reaction at room temperature of 1 mol dipotassium N-cyanodithiocarbamate with 2 mol di-o-tolylguanidine hydrochloride, (IVb) is formed as a fine-crystalline precipitate

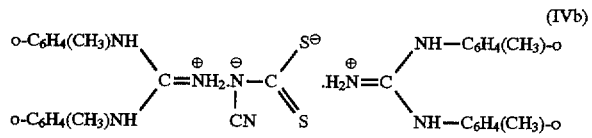

The substances (IIIa), (IVa), (IVb), introduced as accelerators into a rubber compound in the same dosage instead of zinc di-n-butyl dithiocarbamate, which, for example, forms nitrosamine, provide vulcanizates in which N-nitrosamines "typical of rubber" are no longer analytically detectable.

REFERENCE EXAMPLE

As in embodiment (IIIa), the precipitation reaction also occurs between equimolar amounts of DPG-HCl and sodium N,N-dimethyldithiocarbamate, with formation of (IIIb):

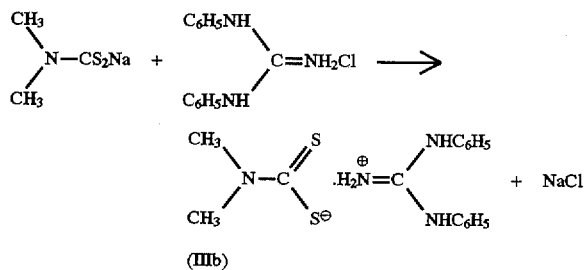

By the replacement of the known nitrosamine-forming accelerator combination zinc dimethyldithiocarbamate plus diphenylguanidine by substance (IIIb), an excellent accelerating action is certainly again observed, but during the vulcanization compound (IIIb), in contrast to compound (IIIa), forms the carcinogenic N-nitrosodimethylamine, which is fundamentally undesirable in the air of workplaces or in consumer articles.

I claim:

1. Salts of formula (III)

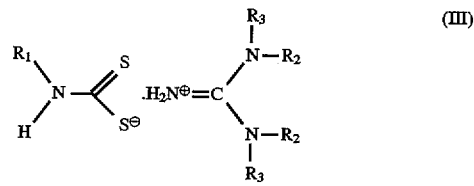

wherein $R_1$ represents CN or a $C_1$–$C_8$ alkyl group, $R_2$ a mononuclear $C_6$–$C_{10}$ aryl group and $R_3$ a $C_1$–$C_3$ alkyl group or hydrogen; and of formula (IV)

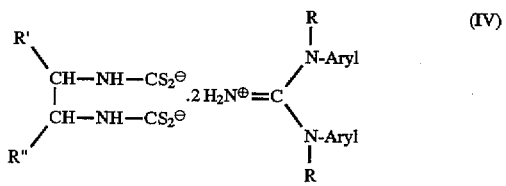

wherein R represents hydrogen or $C_1$–$C_3$ alkyl, Aryl a $C_6$–$C_{10}$ (substituted) phenyl group, and R', R" represent hydrogen and $C_1$–$C_4$ alkyl or R'+R" together represent $C_4$ alkylene.

2. A process for the preparation of the salt according to claim 1, wherein the dithiocarbamate of a primary aliphatic amine, of a bis-amine or of cyanamide is reacted with a guanidine hydrohalide in aqueous solution.

3. A method of accelerating vulcanization of rubber which comprises adding a salt according to claim 1, in which the salt is in the form of a nitrosamine-free vulcanization accelerator.

4. The method of claim 3, wherein $R_1$ is $C_4$ to $C_8$ alkyl, $R_2$ is phenyl, $R_3$ is hydrogen and R' is methyl or hydrogen, R" and R are hydrogen, and Aryl is phenyl or ortho-tolyl.

* * * * *

UNITED STATES PATENT AND TRADEMARK OFFICE
CERTIFICATE OF CORRECTION

PATENT NO. : 5,670,693
DATED : SEPTEMBER 23, 1997
INVENTOR(S) : HERMANN LOHWASSER

It is certified that error appears in the above-identified patent and that said Letters Patent is hereby corrected as shown below:

On the cover page, in section [57] ABSTRACT, "wherein $R^1$" should read --wherein $R_1$--.

In Column 4, line 32 (Claim 1), "R, R'''" should read --R', R''--; Column 4, line 35 (Claim 2), "salt" should be --salts--.

Signed and Sealed this

Ninth Day of December, 1997

Attest:

BRUCE LEHMAN

*Attesting Officer*        Commissioner of Patents and Trademarks